United States Patent
Matsunaga et al.

(10) Patent No.: US 11,491,462 B2
(45) Date of Patent: Nov. 8, 2022

(54) SEA-ISLAND COMPOSITE FIBER, CARRIER FOR ADSORPTION, AND MEDICAL COLUMN PROVIDED WITH CARRIER FOR ADSORPTION

(71) Applicant: TORAY INDUSTRIES, INC., Tokyo (JP)

(72) Inventors: Ryo Matsunaga, Shiga (JP); Junichi Kasuya, Shiga (JP); Yoshiyuki Ueno, Shiga (JP); Hirofumi Yamanaka, Shizuoka (JP); Yasunori Kanemori, Shiga (JP); Masato Masuda, Shizuoka (JP); Joji Funakoshi, Shiga (JP)

(73) Assignee: TORAY INDUSTRIES, INC., Tokyo (JP)

( * ) Notice: Subject to any disclaimer, the term of this patent is extended or adjusted under 35 U.S.C. 154(b) by 464 days.

(21) Appl. No.: 16/625,992

(22) PCT Filed: Aug. 31, 2018

(86) PCT No.: PCT/JP2018/032287
§ 371 (c)(1),
(2) Date: Dec. 23, 2019

(87) PCT Pub. No.: WO2019/045031
PCT Pub. Date: Mar. 7, 2019

(65) Prior Publication Data
US 2021/0154642 A1     May 27, 2021

(30) Foreign Application Priority Data
Aug. 31, 2017 (JP) .............................. JP2017-167355

(51) Int. Cl.
*B01D 15/38* (2006.01)
*B01J 20/26* (2006.01)
(Continued)

(52) U.S. Cl.
CPC .............. *B01J 20/265* (2013.01); *A61M 1/36* (2013.01); *B01D 15/38* (2013.01); *B01J 20/261* (2013.01);
(Continued)

(58) Field of Classification Search
CPC .. B01J 20/265; B01J 20/261; B01J 20/28023; B01J 20/28052; B01J 20/288;
(Continued)

(56) References Cited

FOREIGN PATENT DOCUMENTS

| EP | 0129786 A2 | 1/1985 |
|---|---|---|
| JP | 7-38880 B2 | 5/1995 |

(Continued)

OTHER PUBLICATIONS

Machine translation of JP 2017504733.*
(Continued)

*Primary Examiner* — Benjamin L Lebron
(74) *Attorney, Agent, or Firm* — Birch, Stewart, Kolasch & Birch, LLP

(57) ABSTRACT

An object of the present invention is to provide a ligand-immobilized sea-island composite fiber in which generation of fine particles due to peeling of a sea component from an island component and generation of fine particles due to destruction of a fragile sea component are both suppressed. The present invention provides a sea-island composite fiber comprising a sea component and island components, in which a value (L/S) obtained by dividing the average total length (L) of the perimeter of all island components in a cross section perpendicular to the fiber axis by the average cross-sectional area (S) of the cross section is from 1.0 to 50.0 $\mu m^{-1}$, a distance from the surface to the outermost island component is 1.9 $\mu m$ or less, and an amino group-containing compound is covalently bonded to a polymer (Continued)

constituting the sea component at a charge density of 0.1 μmol or more and less than 500 μmol per 1 gram dry weight.

6 Claims, 1 Drawing Sheet

(51) Int. Cl.
  *B01J 20/28* (2006.01)
  *B01J 20/288* (2006.01)
  *D01F 8/04* (2006.01)
  *A61M 1/36* (2006.01)
(52) U.S. Cl.
  CPC ....... *B01J 20/288* (2013.01); *B01J 20/28023* (2013.01); *B01J 20/28052* (2013.01); *D01F 8/04* (2013.01); *A61M 2202/0401* (2013.01); *A61M 2202/0405* (2013.01); *A61M 2202/0413* (2013.01); *A61M 2202/0415* (2013.01); *A61M 2202/0445* (2013.01); *B01J 2220/445* (2013.01); *B01J 2220/50* (2013.01)
(58) Field of Classification Search
  CPC .. B01J 2220/445; B01J 2220/50; A61M 1/36; A61M 2202/0401; A61M 2202/0405; A61M 2202/0413; A61M 2202/0415; A61M 2202/0445; D01F 8/04
  See application file for complete search history.

(56) References Cited

FOREIGN PATENT DOCUMENTS

| JP | 2004-229867 | A |   | 8/2004  |
|----|-------------|---|---|---------|
| JP | 2007202635  | A | * | 8/2007  |
| JP | 2011194014  | A | * | 10/2011 |
| JP | 2012-5827   | A |   | 1/2012  |
| JP | 2013139647  | A | * | 7/2013  |
| JP | 2014-227633 | A |   | 12/2014 |
| JP | 2015-74853  | A |   | 4/2015  |
| JP | 2017504733  | A | * | 2/2017  |

OTHER PUBLICATIONS

Machine translation of JP 2013139647.*
Machine translation of JP 2011194014.*
Machine translation of JP 2007202635.*
International Search Report, issued in PCT/JP201 8/032287, PCT/ISA/210, dated Oct. 30, 2018.
Written Opinion of the International Searching Authority, issued in PCT/JP2018/032287, PCT/ISA/237, dated Oct. 30, 2018.

* cited by examiner

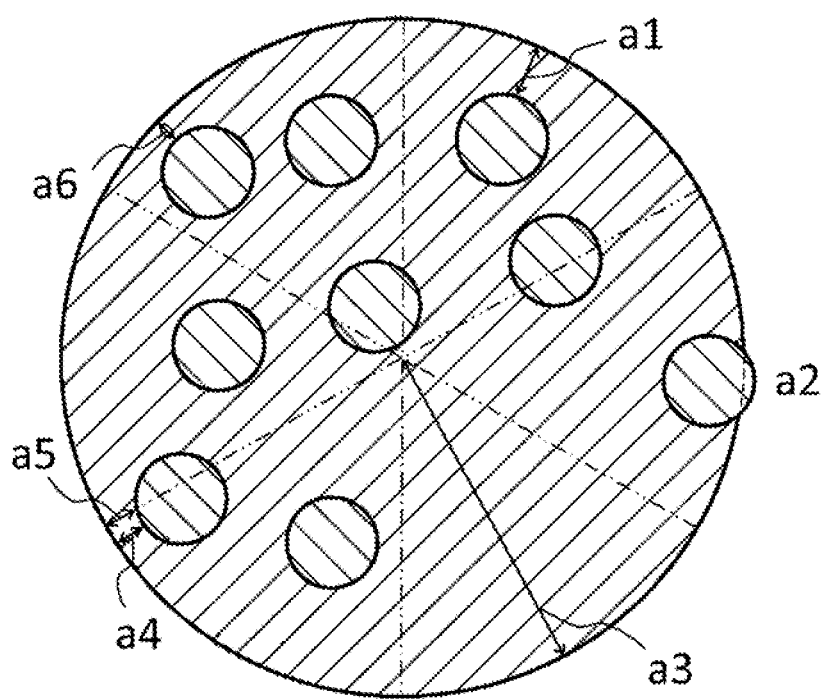

SEA-ISLAND COMPOSITE FIBER, CARRIER FOR ADSORPTION, AND MEDICAL COLUMN PROVIDED WITH CARRIER FOR ADSORPTION

TECHNICAL FIELD

The present invention relates to a sea-island composite fiber, a carrier for adsorption, and a medical column provided with the adsorption carrier.

BACKGROUND ART

Fibers using a thermoplastic polymer are used in a variety of applications because of their excellent mechanical properties and dimensional stability. Since the required characteristics for each application are diverse, when existing polymers cannot meet such requirements, a new polymer with unique properties may be designed and used, and generally, fibers using a composite spinning technique that combines existing polymers are often used. A sensitive effect such as texture or bulkiness and mechanical properties such as strength, elastic modulus, and wear resistance which cannot be achieved with a single polymer fiber can be imparted to a fiber obtained by a composite spinning method, or a so-called composite fiber by, for example, coating a main component with another component. There are a wide variety of composite forms, objective effects and the like for the composite fibers, and various techniques have been proposed according to their applications.

In composite fibers having a variety of forms, many studies have been made on sea-island composite fibers in which a large number of island components are arranged in a sea component, since a wide variety of such products have been developed. Technologies used to obtain ultrafine fibers composed of island components by removing a sea component is commonly seen as an application of sea-island composite fibers, and in some cases, sea-island composite fibers are used as they are for industrial materials such as ropes and cords. There is an example in which a sea-island composite fiber to which molecular adsorption performance is imparted by chemical treatment of a sea component of the fiber is used as a filling carrier for a medical extracorporeal circulation column such as "Toraymyxin (registered trademark)" (manufactured by Toray Industries, Inc.).

Meanwhile, since a fiber has a large specific surface area and can be easily processed, it is suitable as a material having molecular adsorption performance. In Patent Literature 1, a ligand that interacts with endotoxin, which is an adsorption target material, is immobilized on the surface of a fiber. With only a single component polymer, the fiber shape is destroyed by a ligand immobilization reaction, and the polymer becomes powdery. By chemically treating only the sea component of a sea-island composite fiber, a chemical modification reaction is performed, and a chemical-resistant polymer is used as the island component to obtain an adsorbent material in which the fiber form is maintained. In Patent Literature 2, a high mobility group protein adsorption carrier for treating hepatitis is obtained by introducing a functional group having an amino group as a ligand into a sea-island composite fiber.

In Patent Literature 3, by arranging an island component at a certain distance or more on the inner side from the surface of a sea-island composite fiber, the island component is prevented from protruding from a sea component when the sea component is peeled off by a chemical treatment or the like.

Sea-island fiber structures with improved adhesion between a sea component and an island component have also been studied. In order to improve the adhesion between the sea component and the island component, a method of improving the interface area between the sea component and the island component by reducing the diameter of the island component to arrange a large number of island components has been reported. For example, Patent Literature 4 discloses a sea-island composite fiber excellent in durability such as wear resistance or chemical resistance by arranging a large number of island components having a minimum diameter of 0.2 μm densely. In Patent Literature 5, a sea-island composite fiber with improved wear resistance is obtained by controlling the thickness of the sea component present in the outermost layer within a certain range.

CITATION LIST

Patent Literature

Patent literature 1 JP H07-38880 B
Patent literature 2 JP 2012-5827 A
Patent literature 3 JP 2004-229867 A
Patent literature 4 JP 2015-74853 A
Patent literature 5 JP 2014-227633 A

SUMMARY OF INVENTION

Technical Problem

However, when a chemical modification reaction is performed on a polymer material, the polymer material may deteriorate. In particular, as can be seen from the fact that the Japanese Pharmacopoeia stipulates that insoluble fine particles should be tested for pharmaceuticals and medical devices since entry of foreign substances mixed in pharmaceuticals and medical devices into bodies is directly related to their health issues, it is strongly desired that risk of generating foreign particles due to material deterioration is reduced as compared with cases where polymer materials are used for other applications.

In the methods described in Patent Literature 1 and 2, when a ligand immobilization reaction is performed, the sea component deteriorates, an interaction at the interface between the sea component and the island components is attenuated, and the deteriorated fragile sea component may be peeled off from the island components. Furthermore, when the sea component continuously peels off at a wide interface, an island component may protrude from the composite fiber surface. A portion of the sea component that was adjacent to the protruded island component easily peels off, causing generation of fine particles. Patent Literatures 1 and 2 do not refer to anything about a relationship between the fiber volume and the island component surface area, and it cannot be said that a design of a sea-island composite fiber capable of suppressing generation of fine particles is made.

As described in Patent Literature 3, although controlling the thickness of a sea component of the outermost layer to a certain level or more can the peeling of the sea component from the island component, the deteriorated fragile sea component alone exists thickly on the fiber surface. Thus, there is a possibility that the sea component is easily destroyed and fine particles are generated due to mechanical damage that may be caused by a fiber filling process in a column, vibration during transportation and storage, and the like. A fine particle evaluation method described in Patent Literature 3 measures the number of fine particles in a liquid that has passed through a column packed with fibers. In this method, since the mechanical damage given to a fiber is small, generation of fine particles due to destruction of a deteriorated sea component cannot be appropriately evaluated, which is considered problematic from the viewpoint of safety risk evaluation.

Although wear resistance can be improved by the methods described in Patent Literature 4 and 5, an evaluation target in the wear resistance evaluation disclosed here is powders that are generated by friction and can be observed with naked eyes or a magnifier. These powders are considered to be fine particles produced by peeling a sea component that have not undergone chemical modification from an island component in a lump by strong friction, and the inventions of Patent Literatures are not considered to suppress generation of fine particles caused by destruction of the sea component deteriorated by a chemical modification reaction. In other words, there is no prior art that prevents both generation of fine particles due to peeling of a sea component from an island component and generation of fine particles due to destruction of a sea component deteriorated by a chemical modification reaction.

Accordingly, an object of the present invention is to provide a sea-island composite fiber in which generation of fine particles due to peeling of a sea component from an island component and generation of fine particles due to destruction of a fragile sea component deteriorated by a chemical modification reaction are both suppressed.

Solution to Problem

As a result of intensive studies by the present inventors to solve the above problems, the following inventions (1) to (6) have been found.
(1) A sea-island composite fiber comprising a sea component and island components, wherein a value (L/S) obtained by dividing the average total length (L) of the perimeters of all the island components in a cross section perpendicular to the fiber axis by the average cross-sectional area (S) of the cross section is from 1.0 to 50.0 $\mu m^{-1}$, a distance from the surface to the outermost island component is 1.9 µm or less, and an amino group-containing compound is covalently bonded to a polymer constituting the sea component at a charge density of 0.1 µmol or more and less than 500 µmol per 1 gram dry weight.
(2) The sea-island composite fiber according to (1), wherein the L/S is from 1.4 to 50.0 $\mu m^{-1}$.
(3) The sea-island composite fiber according to (1) or (2), wherein a main component of the polymer constituting the sea component is a polymer selected from the group consisting of polystyrene, polysulfone, polymethyl methacrylate, and their derivatives, and a polymer constituting the island components is a polyolefin.
(4) The sea-island composite fiber according to any one of (1) to (3), wherein the amino group-containing compound is ethylenediamine, diethylenetriamine, triethylenetetramine, or tetraethylenepentamine.
(5) A carrier for protein adsorption including the sea-island composite fiber according to any one of (1) to (4).
(6) A medical column including the carrier for protein adsorption according to (5).

Advantageous Effects of Invention

The sea-island composite fiber of the present invention can be used in a wide range of applications because contamination of foreign particles such as fine particles is avoided and it is hardly deteriorated by long-term use. In particular, it can be suitably used as a carrier for protein adsorption for a medical application requiring high safety, and can be used as a filler for a medical column.

BRIEF DESCRIPTION OF DRAWING

FIG. 1 is a view showing a cross section perpendicular to the fiber axis of an example of a sea-island composite fiber.

DESCRIPTION OF EMBODIMENTS

Hereinafter, embodiments of the present invention will be described in more detail. Throughout the present specification, it should be understood that the singular forms also include the plural concept unless specifically stated otherwise. Thus, it should be understood that singular articles (for example, "a", "an", "the", or the like in the case of English) also include the plural concept unless otherwise stated. It should be understood that the terms used in this specification are used in the meaning normally used in the art unless otherwise specified. Thus, unless defined otherwise, all technical and scientific terms used herein have the same meaning as commonly understood by those skilled in the art to which this invention belongs. In case of conflict, the present specification (including definitions) will prevail.

The sea-island composite fiber of the present embodiment is characterized in that a value (L/S) obtained by dividing the average total length (L) of the perimeters of all the island components in a cross section perpendicular to the fiber axis by the average cross-sectional area (S) of the cross section is from 1.0 to 50.0 $\mu m^{-1}$, a distance from the surface to the outermost island component is 1.9 µm or less, and an amino group-containing compound is covalently bonded to a polymer constituting the sea component at a charge density of 0.1 µmol or more and less than 500 µmol per 1 gram dry weight of the sea-island composite fiber.

Sea-island composite fibers are those in which two or more types of polymers having different compositions form a fiber cross section perpendicular to the fiber axis. Here, the sea-island composite fiber has a cross-sectional structure in which an island component made of a polymer is scattered in a sea component made of another polymer. A core-sheath composite fiber is a sea-island composite fiber in which the number of island components ("the number of island components" here is the number of island components scattered in the fiber cross section, also referred to as "the number of islands") is 1. The shape of the sea-island composite fiber is not particularly limited, and is preferably a circular shape because it is not easily damaged by friction. The fiber diameter of a sea-island composite fiber before a chemical modification reaction is preferably from 1 to 50 µm, and more preferably from 2 to 30 µm. The shape of an island component is not particularly limited, and may be any shape such as a circle, an ellipse, a polygon, or a star. In the island component cross section perpendicular to the fiber axis of a sea-island composite fiber, the island components may be formed of two or more types of polymers having different compositions. As the shape of a sea-island composite fiber, among fiber shapes, a yarn bundle, a yarn, a net, a knitted fabric, a woven fabric, and the like processed from the above fiber are preferable, and a yarn bundle, a knitted fabric, and a woven fabric are more preferable in consideration of a large specific surface area and a small channel resistance.

In the sea-island composite fiber of the present embodiment, the number of sea components is preferably one. The number of island components is not particularly limited, and preferably, 50 or more island components are scattered in the sea component because L/S can be increased. On the other hand, if the number of island components is too large, the island components tend to merge after discharge and stable spinning becomes difficult, and therefore, the number of island components is preferably 1,500 or less. In short, the number of island components is preferably 50 to 1,500.

The sea-island composite fiber of the present embodiment can be produced, for example, by spinning using an appropriate sea-island composite die according to the method described in Patent Literature 5, and then carrying out a reaction for introducing an amino group-containing compound described below.

Here, the average total length (L) (μm) of the perimeters of all the island components in a cross section perpendicular to the fiber axis of a sea-island composite fiber, the average cross-sectional area (S) (μm$^2$) in a cross section perpendicular to the fiber axis of a sea-island composite fiber, and the distance from the surface of a sea-island composite fiber to the outermost island component (μm) are obtained as follows.

For a sample obtained by cutting a sea-island composite fiber perpendicular to the longitudinal direction (fiber axis direction) of the fiber, images are taken at 10 randomly selected positions with a scanning electron microscope (SEM) set at a magnification at which island components can be clearly observed. In the obtained image, an area corresponding to one filament is measured in units of μm$^2$, and an average value at 10 positions is defined as an average cross-sectional area (S) (μm$^2$) of a cross section perpendicular to the fiber axis of a sea-island composite fiber.

The perimeters of all the island components (hereinafter also referred to as all island component perimeters) are measured from each image of the fiber cross section taken. The total length of all island component perimeters in each filament is calculated, and the average value of 10 randomly selected positions is defined as the average total length (L) of all island component perimeters in a cross section perpendicular to the fiber axis of a sea-island composite fiber. Note that, when the number of the island components is 150 or more and the variation coefficient of randomly selected 150 island component perimeters is 20% or less, the randomly selected 150 island component perimeters are measured, the total length of all island component perimeters in each filament is calculated by the following formula, and the average value at 10 positions may be the average total length (L) of all island component perimeters.

Total length of all island component perimeters (μm)=Total length of 150 island component perimeters (μm)×number of island components per filament/150

When the value (L/S) obtained by dividing the average total length (L) of the perimeters of all the island components in a cross section perpendicular to the fiber axis of a sea-island composite fiber by the average cross-sectional area (S) of the cross section is high, the island component surface area relative to the fiber volume is increased, the adhesion between the sea component and the island components is increased, peeling of the sea component from island components is suppressed, and the sea component is reinforced, and generation of fine particles due to mechanical damage such as friction is suppressed, which is preferable. On the other hand, when L/S is too high, the island component diameter becomes small, and the durability of the island components decreases. From the above, L/S is from 1.0 to 50.0 μm$^{-1}$, preferably from 1.4 to 50.0 μm$^{-1}$, more preferably from 1.4 to 10.0 μm$^{-1}$, still more preferably from 1.4 to 5.0 μm$^{-1}$, and further more preferably from 1.4 to 4.0 μm$^{-1}$. In other words, L/S is preferably 1.4 μm$^{-1}$ or more. L/S is preferably 10.0 μm$^{-1}$ or less, preferably 5.0 μm$^{-1}$, and preferably 4.0 μm$^{-1}$. Any preferred lower limit value can be combined with any preferred upper limit value. Small average cross-sectional area (S) of a cross section perpendicular to the fiber axis of a sea-island composite fiber is preferable because the inside of the sea-island composite fiber is easily utilized for adsorption, but if the area is too small, the fiber becomes mechanically unstable. Accordingly, the average cross-sectional area (S) is preferably from 1 to 10,000 μm$^2$, more preferably from 10 to 2,500 μm$^2$, and still more preferably from 300 to 1,000 μm$^2$.

In a method of measuring a distance from the surface of a sea-island composite fiber to the outermost island component, an image taken as described above is divided into 6 (two-dot chain lines in FIG. 1) in such a manner to have radial and uniform cross-sectional areas from the center of gravity of a fiber cross section, and the shortest distances (a1 in FIG. 1) from the fiber surface to the outermost island component in each of the divided fiber cross sections are measured to the first decimal place in units of μm. Note that, when the island component protrudes from the fiber surface, the value is 0 μm (a2 in FIG. 1), and when the island component does not exist in the divided fiber cross section, a distance from the center of gravity of the fiber cross section to the fiber surface is measured as the shortest distance (a3 in FIG. 1). When the island component straddles a plurality of divided fiber cross sections and the island component is the outermost island component in the plurality of the divided fiber cross sections, the shortest distances (a4, a5 in FIG. 1) from the fiber surface to the island component in each of the divided fiber cross sections are measured. The average value of the distances measured as described above in each of the divided fiber cross sections (for example, the average value of a1, a2, a3, a4, a5, and a6 in FIG. 1) is defined as a distance from the surface of a sea-island composite fiber to the outermost island component. As the distance from the surface of a sea-island composite fiber to an island component is shorter, the thickness of the surface layer of the fragile sea component deteriorated by chemical modification reaction without a reinforcement component is thinner. Therefore, generation of fine particles due to mechanical damage such as friction is suppressed, which is preferable. From the above, the distance from the surface of a sea-island composite fiber to the outermost island component is 1.9 μm or less, preferably 1.5 μm or less, and more preferably 1.0 μm or less. The lower limit of the distance from the surface of a sea-island composite fiber to the outermost island component is not particularly limited, and may be 0 μm. In other words, the distance from the surface of a sea-island composite fiber to the outermost island component needs to be 0 μm or more and 1.9 μm or less, preferably 0 μm or more and 1.5 μm or less, and more preferably from 0 μm or more to 1.0 μm or less.

In the sea-island composite fiber of the present embodiment, an amino group-containing compound is covalently bonded to a polymer constituting the sea component in order to impart molecular adsorption performance. The "amino group" herein includes a primary amino group, a secondary amino group, a tertiary amino group, and a quaternary ammonium group. The amino group-containing compound is selected from monoamines or polyamines, and examples thereof include monoalkylamines such as ethylamine, propylamine, butylamine, pentylamine, hexylamine, heptylamine, octylamine, nonylamine, and decylamine; dialkylamines such as diethylamine, dipropylamine, dibutylamine, diheptylamine, dioctylamine, and dicyclohexylamine; trialkylamines such as trimethylamine, triethylamine, tripropylamine, tributylamine, tripentylamine, trihexylamine, triheptylamine, trioctylamine, trinonylamine, tridecylamine, and tridodecylamine; polyamines such as ethylenediamine, diethylenetriamine (DETA), triethylenetetramine, tetraethylenepentamine (TEPA), dipropylenetriamine, and polyethyleneimine (PEI). Ethylenediamine, diethylenetriamine, triethylenetetramine, tetraethylenepentamine, dipropylenetriamine, or polyethyleneimine is preferred, ethylenediamine, diethylenetriamine, triethylenetetramine, or tetraethylenepentamine is more preferred, and diethylenetriamine or tetraethylenepentamine is still more preferred. The amino group of the amino group-containing compound covalently bonded to the polymer constituting the sea component may be substituted with other functional group(s).

A sea-island composite fiber in which the amino group-containing compound is covalently bonded to the polymer constituting the sea component includes both a sea-island composite fiber in which the amino group-containing compound is directly covalently bonded to the polymer constituting the sea component and a sea-island composite fiber in which the amino group-containing compound is indirectly bonded to the polymer constituting the sea component via a spacer.

When the above-described polyamine is used as the amino group-containing compound, a plurality of amino groups may be bonded to a sea-island composite fiber to form a crosslinked structure. In other words, in cases where the polyamine is bonded to a sea-island composite fiber as the amino group-containing compound, a crosslinked structure is formed when at least two amino groups in the polyamine are bonded to the sea-island composite fiber.

Here, the polymer constituting the sea component in the sea-island composite fiber and the amino group-containing compound may be directly covalently bonded, or indirectly covalently bonded via a spacer derived from a reactive functional group. The spacer preferably has an electrically neutral chemical bond such as an amide bond, a urea bond, an ether bond, or an ester bond, and more preferably has an amide bond or a urea bond. Two or more amino group-containing compounds may be bonded to one spacer.

Examples of the reactive functional group as a spacer that interposes between the polymer constituting the sea component in the sea-island composite fiber and the amino group-containing compound include an active halogen group such as a halomethyl group, a haloacetyl group, a haloacetamidomethyl group, or a halogenated alkyl group, an epoxide group, a carboxyl group, an isocyanate group, a thioisocyanate group, or an acid anhydride group. From the viewpoint of having an appropriate reactivity, an active halogen group (particularly a haloacetyl group) is preferable, and a haloacetamidomethyl group is more preferable. Specific examples of the polymer constituting the sea component in a sea-island composite fiber in which a reactive functional group is introduced include polystyrene to which a chloroacetamidomethyl group is added, and polysulfone to which a chloroacetamidomethyl group is added. These polymers are soluble in organic solvents and have the advantage of being easy to mold.

The reactive functional group can be introduced in advance by reacting with the polymer constituting the sea component in a sea-island composite fiber. For example, when the polymer constituting the sea component is polystyrene and the reactive functional group is a chloroacetamidomethyl group, a reaction of polystyrene with N-methylol-α-chloroacetamide can provide polystyrene to which chloroacetamidomethyl group is introduced. Then, the amino group-containing compound (for example, diethylenetriamine or tetraethylenepentamine) is reacted with the above-described polystyrene to which chloroacetamidomethyl group is introduced, thereby can form a covalent bond. In this case, the acetamidomethyl group is the spacer that interposes between the polymer (polystyrene) constituting the sea component in the sea-island composite fiber and the amino group-containing compound.

The amino group-containing compound is preferably covalently bonded to the polymer constituting the sea component on the surface of a sea-island composite fiber.

From the viewpoint that a covalent bond formation reaction with the sea component on the surface of a sea-island composite fiber can be easily performed via a reactive functional group, the amino group-containing compound is more preferably covalently bonded to the polymer constituting the sea component on the surface of a sea-island composite fiber via a spacer.

From the viewpoint of immunosuppressive protein adsorption performance, it is preferable that an amino group-containing compound covalently bonded to a polymer constituting a sea component has a high charge density, but when the density is too high, undesirable non-specific adsorptive properties against, for example, blood anticoagulants (such as heparin) increase. When used for blood purification therapy, it is known that a carrier having a high heparin adsorptivity has problems such as difficulty in controlling the blood heparin concentration during treatment (JP H05-329364). Therefore, the charge density of an amino group-containing compound covalently bonded to a polymer constituting a sea component per gram dry weight of the sea-island composite fiber is 0.1 µmol or more and less than 500 µmol, preferably 10 µmol or more and less than 500 µmol, more preferably 10 µmol or more and 350 µmol or less, and still more preferably 20 µmol or more and 350 µmol or less. In other words, the charge density of an amino-group-containing compound covalently bonded to a polymer constituting a sea component is preferably 10 µmol or more per 1 gram dry weight of the sea-island composite fiber, and preferably 20 µmol or more per 1 gram dry weight of the sea-island composite fiber. The charge density of an amino group-containing compound covalently bonded to a polymer constituting a sea component is preferably 350 µmol or less per 1 g dry weight of a sea-island composite fiber. Any preferred lower limit can be combined with any preferred upper limit. When measuring the charge density, a sea-island composite fiber is used in a dried state. Here, the dried state refers to a state where the amount of a liquid component contained in a sea-island composite fiber is 1% by weight or less, and when the amount of decrease in the weight of a remaining fiber dried after measuring the weight for 12 hours in a vacuum dryer at room temperature (0.06 atm or less) is 1% by weight or less of the weight of the fiber before drying, the fiber is considered dry.

For example, acid-base titration can be used as a method of measuring the charge density of a sea-island composite fiber per 1 gram dry weight.

The above-described preferable value (L/S) obtained by dividing the average total length (L) of the perimeters of all the island components in a cross section perpendicular to the fiber axis of a sea-island composite fiber by the average cross-sectional area (S) of the cross section, the above-described preferable distance from the surface of a sea-island composite fiber to the outermost island component, and the above-described preferable charge density of an amino group-containing compound covalently bonded to a polymer constituting a sea component may be freely combined. One embodiment includes a sea-island composite fiber comprising a sea component and island components, wherein a value (L/S) obtained by dividing the average total length (L) of the perimeters of all the island components in a cross section perpendicular to the fiber axis by the average cross-sectional area (S) of the cross section is from 1.4 to 10.0 $\mu m^{-1}$, a distance from the surface to the outermost island component is 1.9 µm or less, and an amino group-containing compound is covalently bonded to a polymer constituting the sea component at a charge density of 10 µmol or more and less than 500 µmol per 1 gram dry weight. Another embodiment includes a sea-island composite fiber comprising a sea component and island components, wherein a value (L/S) obtained by dividing the average total length (L) of the perimeters of all the island components in a cross section perpendicular to the fiber axis by the average cross-sectional area (S) of the cross section is from 1.4 to 4.0 $\mu m^{-1}$, a distance from the surface to the outermost island component is 1.5 µm or less, and an amino group-containing compound is covalently bonded to a polymer constituting the sea component at a charge density of 10 µmol or more and 350 µmol or less per 1 gram dry weight.

The polymer constituting the island component is not particularly limited, and for example, polyethylene terephthalate, a copolymer obtained by copolymerizing polyethylene terephthalate with at least one selected from the group consisting of phthalic acid, isophthalic acid, 5-sodium sulfoisophthalic acid, adipic acid, sebacic acid, 1,4-butanediol, diethylene glycol, polyethylene glycol or ε-caprolactone, and lactic acid, liquid crystal polyester such as polyarylate, a polymer that can be melt molded such as polyethylene naphthalate, polyphenylene sulfide, polybutylene terephthalate, polytrimethylene terephthalate, polystyrene, polyolefin, polycarbonate, polyacrylate, polyamide, polylactic acid, or thermoplastic polyurethane, or a polymer alloy thereof is preferably used. Among these, polyolefins such as polyethylene or polypropylene are preferable from the viewpoint of chemical resistance, and polypropylene is more preferable.

The main component of the polymer constituting the sea component is not particularly limited as long as the component can bind an amino group-containing compound, and for example, a polymer selected from the group consisting of polystyrene, polysulfone, polymethyl methacrylate, and derivatives thereof, specifically, a homopolymer of polystyrene, poly-α-methyl styrene, polychloromethylstyrene, polyethersulfone, polysulfone, polyarylethersulfone, chloromethylated polysulfone, or polymethylmethacrylate, a copolymer obtained by combining two or more of the above polymers, or a copolymer of any one of the monomers constituting the polymer and a monomer other than the monomer constituting the polymer, whose main component is any one of the above polymers (for example, acrylonitrile/styrene copolymer), or a polymer alloy of any one of the polymers and a polymer other than the polymer, whose main component is any one of the above polymers (for example, a polymer alloy of polystyrene and polypropylene) can be used. In particular, a polymer alloy of polystyrene and polyolefin whose main component is polystyrene (for example, a polymer alloy of polystyrene and polyethylene whose main component is polystyrene, or a polymer alloy of polystyrene and polypropylene whose main component is polystyrene) is more preferable from the viewpoint of having chemical resistance and easily maintaining the physical shape. Among them, a polymer alloy of polystyrene and polypropylene having polystyrene as a main component is more preferable. Here, the main component means a component having the highest weight ratio among constituent polymers.

The types of the polymer constituting the island component and the types of the polymer constituting the sea component may be freely combined. For example, the main component of the polymer constituting the sea component is a polymer selected from the group consisting of polystyrene, polysulfone, polymethyl methacrylate, and derivatives thereof, and the polymer constituting the island component is polyolefin. In particular, it is preferred that the polymer constituting the sea component is a polymer alloy of polystyrene and polypropylene whose main component is polystyrene, and the polymer constituting the island component is polypropylene. When the type of the polymer constituting the island component and the type of the polymer constituting the sea component are the same, a sea-island composite fiber cannot be constituted, and therefore, the polymer constituting the island component and the polymer constituting the sea component need to have different compositions or different constituent ratios.

Examples of the method of evaluating peeling of the sea component from the island component include a method of measuring the extent of the exposure of the island component by SEM observation.

Examples of the method of evaluating fine particle generation due to friction include a method of measuring the number of fine particles in water generated by rotating a stirring bar on a test fiber knitted fabric in water to produce friction.

The carrier for protein adsorption of the present invention is also characterized by containing the above-described sea-island composite fiber.

Since generation of fine particles is suppressed, the sea-island composite fiber of the present embodiment can be widely used in applications where contamination with foreign substances should be avoided or where long-term use is required without deterioration. In particular, the sea-island composite fiber can be suitably used as an adsorbing carrier for a medical application that requires high safety, especially as a carrier for protein adsorption (in particular, a carrier for adsorption of a cytokine such as latent transforming growth factor-β).

The "carrier for adsorption" means a carrier capable of adsorbing and removing a biological component (for example, proteins or cells).

The shape of carrier for adsorption is preferably a yarn bundle, a knitted fabric, and a woven fabric, and particularly preferably a knitted fabric in consideration of a large specific surface area and a small channel resistance.

The "medical application" means an application used for treatment of diseases, and examples thereof include a body fluid purification application and an artificial organ application. In particular, the sea-island composite fiber of the present embodiment is preferably used for a body fluid purification application, since the fiber is excellent in the molecule adsorption performance. Examples of the body fluid purification application include a protein adsorption application, a small molecule adsorption application, and a cell adsorption application, and the protein adsorption application is more preferable in that the application can be expected to exhibit the molecular adsorption performance of the sea-island composite fiber of the present embodiment most.

The "protein" means a structure containing, as a component, a molecule in which a large number of amino acids are linked by peptide bonds, and examples thereof include an albumin, an immunoglobulin, and a cytokine. Here, "cytokine" means a protein used for information transmission of an immune cell, and examples thereof include interleukin, tumor necrosis factor-α, latent transforming growth factor-β (hereinafter, latent TGF-β), angiogenic growth factor, immunosuppressive acidic protein. As an adsorption target, a cytokine is preferable from the viewpoint that recovery of immune status can be expected, and latent TGF-β is more preferable from the viewpoint that it can cancel an immunosuppressive state and is expected to be effective for cancer treatment.

Examples of the method of determining the protein adsorption performance of a carrier for adsorption include a method of determining the amount of adsorption per knitted fabric weight by adding a certain weight of a knitted fabric composed of a sea-island composite fiber to a protein solution of a certain concentration and a certain volume, mixing for a certain period of time, measuring protein concentrations in the solution before loading the carrier and after mixing, and dividing the calculated protein reduction by the weight of the knitted fabric used. Examples of the method of measuring the protein concentration include an enzyme-linked immuno-sorbent assay (ELISA) method.

The medical column of the present invention is characterized by including the above-described carrier for protein adsorption.

The "column" means one including at least a blood inlet portion, a case portion, and a blood outlet portion, wherein the case portion is filled with a carrier for adsorption. Examples of the column include a radial flow type column.

Since the medical column can adsorb a substance from a liquid by passing the liquid therethrough, the column can be used for purifying or removing a target substance from a liquid containing a multi-component substance, and for example, can be used for separation or the like of a biological component. The medical column is particularly suitable for a column for body fluid purification. Here, the column for body fluid purification refers to a column having a function of removing a waste product or a harmful substance in a body fluid such as blood, plasma, serum, ascites, lymph, or joint fluid by circulating the body fluid extracorporeally. Among columns for body fluid purification, columns for blood purification are preferably used because such columns are widely utilized for the purpose of removing a specific blood cell component, a protein, a toxin derived from a microorganism, or the like from peripheral blood, and particularly preferably used for the purpose of adsorbing proteins. Among proteins, cytokines such as interleukins, tumor necrosis factor-α, latent TGF-β, angiogenic growth factors, and immunosuppressive acidic proteins are used for information transmission of immune cells, and removal of these from a body fluid (especially, a blood) can recover immune status, and therefore, these cytokines are suitable as adsorption targets.

Examples of the method of evaluating the performance of the medical column include a method of measuring the amount of a protein adsorbed. A latent TGF-β is preferable as an adsorption target from the viewpoint that it can cancel an immunosuppressive state and is expected to be effective for cancer treatment.

The medical column of the present embodiment can efficiently adsorb proteins from blood using it as a column for extracorporeal circulation. In particular, since recovery of immune status can be expected by removing proteins such as cytokines, the medical column is preferably used as a column for cancer treatment.

EXAMPLES

The present invention will now be described with reference to Examples, but is not limited thereto. For each Example and Comparative Example, the following treatments and evaluations were performed.

A. Introduction of the Amino Group-Containing Compound into the Polymer Constituting the Sea Component:

40 mL of a reaction solution (hereinafter, referred to as NMCA reaction solution) was prepared by mixing, based on 1 g of a cylindrical knitted fabric obtained by knitting a sea-island composite fiber, 46% by weight of nitrobenzene, 46% by weight of sulfuric acid, 1% by weight of paraformaldehyde, and 7% by weight of N-methylol-α-chloroacetamide (NMCA) at 10° C. or less, and the knitted fabric was immersed in the NMCA reaction solution and allowed to react at 4° C. for 2 hours. The knitted fabric was then taken out of the reaction solution, and immersed in nitrobenzene in the same amount as the NMCA reaction solution and washed. Subsequently, the knitted fabric was taken out, immersed in methanol and washed to obtain an α-chloroacetamidomethylated knitted fabric (hereinafter, referred to as "knitted fabric of intermediate 1"). A solution in which an amino group-containing compound was dissolved in 96% by weight of dimethyl sulfoxide (DMSO) and 4% by weight of triethylamine (hereinafter, amination reaction solution) was prepared (compound type, compound concentration, and liquid amount are described below for each Example and Comparative Example), and the knitted fabric of intermediate 1 was immersed in the amination reaction solution and allowed to react at 30° C. for 3 hours. Thereafter, the knitted fabric was taken out from the reaction solution, and immersed in DMSO in the same amount as the reaction solution and washed. Subsequently, the knitted fabric was taken out and washed by immersing in methanol and then water to obtain an aminated knitted fabric.

B. Evaluation of the Average Total Length (L) of the Perimeters of all Island Components in a Cross Section Perpendicular to the Fiber Axis of a Sea-Island Composite Fiber, the Average Cross-Sectional Area (S) in a Cross Section Perpendicular to the Fiber Axis of a Sea-Island Composite Fiber, and the Distance from the Surface of a Sea-Island Composite Fiber to the Outermost Island Component:

For a sample obtained by cutting the sea-island composite fiber perpendicular to the longitudinal direction (fiber axis direction), images are taken at 10 positions for each fiber with a scanning electron microscope (SEM)S-5500 (manufactured by Hitachi High-Technologies Corporation) set at a magnification at which the island components can be clearly observed. In the obtained images, areas corresponding to one filament is measured in units of $\mu m^2$ to the first decimal place, and the average value at 10 positions was rounded off to the whole number to obtain a value, which was defined as the average cross-sectional area (S) of the cross section perpendicular to the fiber axis of the sea-island composite fiber in each Example and Comparative Example. From these images, the perimeters of all the island components were measured in $\mu m$ to the second decimal place using image processing software ImageJ version 1.50i (created by National Institutes of Health). The total length of the perimeters of all the island components for each filament was calculated, and the average value at 10 positions was rounded off to the whole number to obtain a value, which was defined as the average total length (L) of the perimeters of all the island components of the cross section perpendicular to the fiber axis of the sea-island composite fiber in each Example and Comparative Example. Note that, when the number of the island components is 150 or more, and the variation coefficient of the perimeters of 150 island components randomly selected is 20% or less, the perimeters of randomly extracted 150 island components was measured in units of μm to the second decimal place, and the total length of the perimeters of all the island components for each filament was calculated using the following formula, and the average value at 10 positions was rounded off to the whole number to obtain a value, which was defined as the average total length (L) of the above-described perimeters of all the island components in each Example and Comparative Example.

>Total length of perimeters of all the island components=Total length of perimeters of 150 island components×number of the island components per filament/150

L/S was calculated by rounding off the second decimal place to the first decimal place.

The distance from the surface of the sea-island composite fiber to the outermost island component was measured for each of the fiber cross-sectional images taken at 10 positions according to the above method, and the average value at 10 positions was defined as the distance from the surface of the sea-island composite fiber to the outermost island component in each Example and Comparative Example.

C. Evaluation of the Island Component Exposure:

The surface of a sea-island composite fiber was observed with a scanning electron microscope (SEM)S-5500 (manufactured by Hitachi High-Technologies Corporation) at 200 times magnification. For each fiber, a plurality of images were taken in such a manner that the total area of portions where the fiber surface could be clearly observed was 1 mm$^2$ or more. From these images, the area of a portion where the fiber surface can be clearly observed was measured in units of mm$^2$ to the third decimal place using image processing software ImageJ version 1.50i (created by National Institutes of Health), and in that portion, the number (the number of exposed island components) of locations where an island component protrudes from the fiber surface and is exposed was counted. This was performed using a plurality of images until the total area exceeded 1 mm$^2$, and the numbers of locations where an island component was exposed was totaled. A value obtained by dividing the total number of the exposed island components by the total area of the analyzed portions and rounding off the first decimal place was defined as the island component exposure (unit: pieces/mm$^2$), and two-level evaluation was performed based on the following criteria. If the island component exposure is less than 20 pieces/mm$^2$, it is considered that the island components hardly protrude on the appearance of the composite fiber surface, and the sea component is hardly peeled off.

○: less than 20 pieces/mm$^2$
×: 20 pieces/mm$^2$ or more

D. Measurement of the Charge Density:

The charge density of the amino group-containing compound covalently bonded to the polymer constituting the sea component was measured by the following method. A knitted fabric composed of about 0.5 g of sea-island composite fibers was immersed in 40 mL of 6 M aqueous sodium hydroxide solution and mixed for 15 minutes. This knitted fabric was taken out and immersed in water several times and mixed and washed until the pH of the solution reached 7. The washed knitted fabric was dried for 12 hours or longer in a vacuum dryer (0.06 atm or less) at room temperature, and the weight after drying was measured (this is defined as W [g]). The knitted fabric after drying was immersed in 40 mL of 0.01 M hydrochloric acid and mixed for 30 minutes. 5 mL of this liquid was sampled, an appropriate amount of phenolphthalein liquid was added, and titrated with a 0.005 M aqueous sodium hydroxide solution. This titration operation was performed three times, and the amount of 0.005 M sodium hydroxide aqueous solution required for each titration was measured in mL to the second decimal place, and the average value was defined as A [mL]. The charge density of the amino group-containing compound was calculated by the following formula, and the value was obtained by rounding off the first decimal place. Hereinafter, the charge density of the amino group-containing compound covalently bonded to the polymer constituting the sea component per 1 g dry weight of the sea-island composite fiber is expressed in units of μmol/g. Charge density [μmol/g]={(5 [mL]×0.01 [M]−A [mL]×0.005 [M])×(40 [mL]/5 [mL])×10$^3$}/W [g]

E. Evaluation of the Number of the Fine Particles Generated:

The knitted fabric composed of the sea-island composite fibers having a basis weight in a dry state of about 100 g/m$^2$ was cut out into a circular shape with a diameter of 26 mm in a wet state, put into a clean container together with 50 mL of ion-exchanged water (filtered water) passed through a HEPA filter with a pore size of 0.3 μm, and mixed by inverting 10 times, and then the liquid was discharged, and fiber waste produced from the knitted fabric end surface was washed. This washing operation was repeated 5 times. The washed test knitted fabric was placed on a base plate attached to a stirring-type ultra-holder UHP-25K (manufactured by Advantec Toyo Kaisha, Ltd.), an O-ring was stacked, and then sandwiched between cylindrical containers (cells) having a diameter of 18 mm, and fixed with a base mounting bracket. The liquid outlet of the base plate was closed with a silicone tube, 10 mL of filtered water was added with the knitted fabric on the bottom side, and it was confirmed that there was no water leakage. A stirring set attached to UHP-25K was attached thereto, and stirring was carried out on a magnetic stirrer RCN-7 (manufactured by Tokyo Rika Kikai Co., Ltd.) for 5 minutes at a rotation speed of 600 rpm with the stirring set not contacting the knitted fabric. This liquid was collected, 3 mL was measured by a light-shielding-type automatic particle measuring device KL-04 (manufactured by RION Co., Ltd.), and washing operation by stirring was repeated by changing filter water until the number of fine particles of 5 μm or more per mL was 30 or less. Thereafter, the liquid in the cell was completely discharged, the stirring set was removed, a 14 mm-diameter crosshead-type PTFE stirrer (manufactured by SANPLATEC CO., LTD.) was placed in the cell, and 10 mL of filtered water was further added into the cell. The stirrer was adjusted on the magnetic stirrer so as to be positioned at the center of the cylinder, and the stirrer was stirred for 5 minutes at a rotation speed of 600 rpm in such a manner that the stirrer rubs the knitted fabric. This liquid was collected, 3 mL was measured by a light-shielding-type automatic particle measuring device, and the number of particles of 5 μm or more per mL was defined as the number of generated particles (unit: pieces/mL).

Two-level evaluation was performed according to the following criteria. If the number of fine particles generated is less than 200 pieces/mL, it is considered that the wear resistance is almost the same as that of a ligand-unimmobilized fiber.

○: less than 200 pieces/mL
×: 200 pieces/mL or more

F. Evaluation of Protein Adsorption Performance:

The adsorption target material was determined as latent TGF-β, and the adsorption performance was evaluated in a solution in which latent TGF-β was added to 3.5% by weight of bovine serum albumin (BSA)-containing phosphate buffered saline (PBS) that mimics blood. The knitted fabric composed of the test sea island composite fiber with a dry knitted fabric weight of about 40 mg was immersed in a PBS solution in which 25 ng/mL latent TGF-β and 3.5% by weight of BSA (manufactured by Merck Millipore) are dissolved (Dulbecco PBS (-) manufactured by NISSUI PHARMACEUTICAL CO., LTD.) (hereinafter, latent TGF- solution) at a rate of 25 mL per gram of the dry knitted fabric, and mixed by inversion in a 37° C. incubator using a rotator for 2 hours. The knitted fabric composed of the sea-island composite fiber was then taken out, the concentration of latent TGF-β in the latent TGF-β solution was quantified using Human TGF-β1 Quantikine ELISA Kit (manufactured by R & D Systems), and the value was calculated to the first decimal place by rounding off the second decimal place in units of ng/mL. In accordance with the following formula, the amount of latent TGF-β adsorbed per knitted fabric weight was calculated, and the obtained value was rounded off to the whole number.

Latent TGF-β adsorption amount per knitted fabric weight [ng/g]=(Latent TGF-β concentration [ng/mL] before adsorption reaction)−latent TGF-β concentration [ng/mL] after adsorption reaction)×latent TGF-β solution amount [mL]/dry knitted fabric weight [g]

Two-level evaluation was performed according to the following criteria.
  ○: 20 ng/g or more
  x: less than 20 ng/g Comparative Example 1, Examples 1 to 4

A polymer alloy composed of 90% by weight of polystyrene and 10% by weight of polypropylene as the sea component and polypropylene as the island component were separately melted and metered into a spinning pack incorporating a sea-island composite spinneret having 704 island component distribution holes per discharge hole to form a sea-island composite flow, and melted and discharged. The sea-island composite fiber (hereinafter, referred to as the sea-island composite fiber of Comparative Example 1) was collected by controlling the island ratio to 50% by weight. The fiber diameter was 20 μm. Further, α-chloroacetamidomethylated knitted fabric (hereinafter, referred to as knitted fabric of Comparative Example 2) was obtained according to the method described in "A. Introduction of the amino group-containing compound into the polymer constituting the sea component", using the collected sea-island composite fiber of Comparative Example 1 as a knitted fabric (hereinafter, the knitted fabric of Comparative Example 1). Further, 68 mL of an amination reaction solution (diethylenetriamine (DETA) was dissolved as an amino group-containing compound) per 1 g of the knitted fabric of Comparative Example 2 was reacted at various concentrations to obtain each aminated knitted fabric (hereinafter, the knitted fabrics of Examples 1 to 4, respectively). The amination reaction solution was used after adjusting the DETA concentration to 0.1 mM (knitted fabric of Example 1), 1 mM (knitted fabric of Example 2), 2 mM (knitted fabric of Example 3), and 4 mM (knitted fabric of Example 4), respectively. Various tests were performed using the obtained knitted fabric of Comparative Example 1, the knitted fabric of Comparative Example 2, and the knitted fabrics of Examples 1 to 4. The sea-island composite fibers constituting each knitted fabric were analyzed and measured for the L/S, the distance from the fiber surface to the outermost island component, and the island component exposure. The results are shown in Tables 1 and 2. The L/S measurement results were 3.7 μm$^{-1}$ for the knitted fabric of Comparative Example 1, 3.1 μm$^{-1}$ for the knitted fabric of Comparative Example 2, and from 2.6 to 3.2 μm$^{-1}$ for the knitted fabrics of Examples 1 to 4. The distances from the fiber surface to the outermost island component were 0.9 μm or less in all cases. The island component exposures were 2 pieces/mm$^2$ or less in all cases. The numbers of fine particles generated were 153 pieces/mL or less in all cases. The charge densities of the knitted fabric of Comparative Example 1 and the knitted fabric of Comparative Example 2 that were not aminated were both 0 μmol/g. The knitted fabrics of Examples 1 to 4 subjected to amination had a charge density of from 11 to 324 μmol/g, and the charge densities increased according to the DETA concentration during the amination reaction. The latent TGF-β adsorption amount was 5 ng/g for the knitted fabric of Comparative Example 1, 17 ng/g for the knitted fabric of Comparative Example 2, and from 34 to 79 ng/g for the knitted fabrics of Examples 1 to 4 reacted with DETA. The reason why the amount of latent TGF-β adsorption increased in the knitted fabrics of Examples 1 to 4 compared to the knitted fabric of Comparative Example 2 is thought to be due to an electrostatic interaction between the negatively charged portion of latent TGF-β and the positive charge of the amino group introduced on the fiber surface.

Example 5

An aminated knitted fabric (hereinafter, knitted fabric of Example 5) was obtained by the same treatment as that of the knitted fabric of Example 2 except that tetraethylenepentamine (TEPA) having a concentration of 1 mM instead of DETA was used as the amino group-containing compound in the amination reaction solution. Various tests were performed using the obtained knitted fabric of Example 5. The results are shown in Tables 1 and 2. L/S was 2.9 μm$^{-1}$, the distance from the fiber surface to the outermost island component was 0.7 μm, and the charge density was 187 μmol/g. The island component exposure was 3 pieces/mm$^2$, the number of fine particles was 133 pieces/mL, and the latent TGF-β adsorption amount was 66 ng/g.

Example 6

An aminated knitted fabric (hereinafter, knitted fabric of Example 6) was obtained by the same treatment as that of the knitted fabric of Example 2 except that polyethyleneimine (PEI, number average molecular weight about 10,000) having a concentration of 0.2% by weight instead of DETA was used as the amino group-containing compound in the amination reaction solution. Various tests were performed using the obtained knitted fabric of Example 6. The results are shown in Tables 1 and 2. L/S was 3.2 μm$^{-1}$, the distance from the fiber surface to the outermost island component was 1.1 μm, and the charge density was 261 μmol/g. The island component exposure was 1 pieces/mm$^2$, the number of fine particles was 101 pieces/mL, and the latent TGF-β adsorption amount was 58 ng/g.

Comparative Examples 3, 4, Example 7

A polymer alloy composed of 90% by weight of polystyrene and 10% by weight of polypropylene as the sea component and polypropylene as the island component were separately melted and metered into a spinning pack incorporating a sea-island composite spinneret having 1024 island component distribution holes per discharge hole to form a sea-island composite flow and melted and discharged. The sea-island composite fiber (hereinafter, referred to as the sea-island composite fiber of Comparative Example 3) was collected by controlling the island ratio to 50% by weight. The fiber diameter was 23 Further, α-chloroacetamidomethylated knitted fabric (hereinafter, referred to as knitted fabric of Comparative Example 4) was obtained according to the method described in "A. Introduction of the amino group-containing compound into the polymer constituting the sea component", using the collected sea-island composite fiber of Comparative Example 3 as a knitted fabric (hereinafter, knitted fabric of Comparative Example 3). Further, 43 mL of an amination reaction solution with a DETA concentration of 1 mM per 1 g of the knitted fabric of Comparative Example 4 was used to obtain an aminated knitted fabric (hereinafter, a knitted fabric of Example 7). Various tests were performed using the obtained knitted fabric of Comparative Example 3, the knitted fabric of Comparative Example 4, and the knitted fabric of Example 7. The results are shown in Tables 1 and 2. The L/S values were from 2.7 to 3.7 $\mu m^{-1}$, and the distances from the fiber surface to the outermost island component were 0.1 μm in all cases. The charge densities of the knitted fabric of Comparative Example 3 and the knitted fabric of Comparative Example 4 were 0 μmol/g, and the charge density of the knitted fabric of Example 7 was 497 μmol/g. The island component exposures were 8 pieces/mm$^2$ or less in all cases. The numbers of fine particles generated were 96 pieces/mL or less in all cases. The latent TGF-β adsorption amounts were 1 ng/g for the knitted fabric of Comparative Example 3, 13 ng/g for the knitted fabric of Comparative Example 4, and 140 ng/g for the knitted fabric of Example 7 reacted with DETA.

Comparative Examples 5, 6, Example 8

A polymer alloy composed of 90% by weight of polystyrene and 10% by weight of polypropylene as the sea component and polypropylene as the island component were separately melted and metered into a spinning pack incorporating a sea-island composite spinneret having 704 island component distribution holes per discharge hole to form a sea-island composite flow and melted and discharged. The sea-island composite fiber (hereinafter, referred to as a sea-island composite fiber of Comparative Example 5) was collected by controlling the island ratio to 50% by weight. The fiber diameter was 30 μm. Further, α-chloroacetamidomethylated knitted fabric (hereinafter, referred to as knitted fabric of Comparative Example 6) was obtained according to the method described in "A. Introduction of the amino group-containing compound into the polymer constituting the sea component", using the collected sea-island composite fiber of Comparative Example 5 as a knitted fabric (hereinafter, knitted fabric of Comparative Example 5). Further, 43 mL of an amination reaction solution with a DETA concentration of 1 mM per 1 g of the knitted fabric of Comparative Example 6 was used to obtain an aminated knitted fabric (hereinafter, a knitted fabric of Example 8). Various tests were performed using the obtained knitted fabric of Comparative Example 5, the knitted fabric of Comparative Example 6, and the knitted fabric of Example 8. The results are shown in Tables 1 and 2. The L/S values were from 1.9 to 2.5 $\mu m^{-1}$, and the distances from the fiber surface to the outermost island component were from 1.9 to 2.1 μm. The charge densities of the knitted fabric of Comparative Example 5 and the knitted fabric of Comparative Example 6 were 0 μmol/g, and the charge density of the knitted fabric of Example 8 was 211 μmol/g. The island component exposures were 0 pieces/mm$^2$ in all cases. The numbers of fine particles generated were 190/mL or less in all cases. The latent TGF-β adsorption amounts were 5 ng/g for the knitted fabric of Comparative Example 5, 13 ng/g for the knitted fabric of Comparative Example 6, and 71 ng/g for the knitted fabric of Example 8 reacted with DETA.

Comparative Examples 7 to 9

A polymer alloy composed of 90% by weight of polystyrene and 10% by weight of polypropylene as the sea component and polypropylene as the island component were separately melted and metered into a spinning pack incorporating a sea-island composite spinneret having 1024 island component distribution holes per discharge hole to form a sea-island composite flow and melted and discharged. The sea-island composite fiber (hereinafter, referred to as the sea-island composite fiber of Comparative Example 7) was collected by controlling the island ratio to 50% by weight. The fiber diameter was 30 μm. Further, α-chloroacetamidomethylated knitted fabric (hereinafter, referred to as the knitted fabric of Comparative Example 8) was obtained according to the method described in "A. Introduction of the amino group-containing compound into the polymer constituting the sea component", using the collected sea-island composite fiber of Comparative Example 7 as a knitted fabric (hereinafter, knitted fabric of Comparative Example 7). Further, 43 mL of an amination reaction solution with a DETA concentration of 1 mM per 1 g of the knitted fabric of Comparative Example 8 was used to obtain an aminated knitted fabric (hereinafter, a knitted fabric of Comparative Example 9). Various tests were performed using the obtained knitted fabric of Comparative Example 7, the knitted fabric of Comparative Example 8, and the knitted fabric of Comparative Example 9. The results are shown in Tables 3 and 4. The L/S values were from 2.4 to 3.0 $\mu m^{-1}$, and the distances from the fiber surface to the outermost island component were from 2.2 to 2.4 μm. The charge densities of the knitted fabric of Comparative Example 7 and the knitted fabric of Comparative Example 8 were 0 μmol/g, and the charge density of the knitted fabric of Comparative Example 9 was 162 μmol/g. The island component exposures were 0 pieces/mm$^2$ in all cases. The numbers of fine particles generated were 36 pieces/mL for the knitted fabric of Comparative Example 7, and 394 pieces/mL and 355 pieces/mL for the knitted fabric of Comparative Example 8 and the knitted fabric of Comparative Example 9, respectively. The latent TGF-β adsorption amounts were 0 ng/g for the knitted fabric of Comparative Example 7, 14 ng/g for the knitted fabric of Comparative Example 8, and 90 ng/g for the knitted fabric of Comparative Example 9 reacted with DETA.

Comparative Examples 10 to 12

A polymer alloy composed of 90% by weight of polystyrene and 10% by weight of polypropylene as the sea component and polypropylene as the island component were separately melted and metered into a spinning pack incorporating a sea-island composite spinneret having 16 island component distribution holes per discharge hole to form a sea-island composite flow and melted and discharged. The sea-island composite fiber (hereinafter, referred to as a sea-island composite fiber of Comparative Example 10) was collected by controlling the island ratio to 50% by weight. The fiber diameter was 20 µm. Further, α-chloroacetamidomethylated knitted fabric (hereinafter, referred to as knitted fabric of Comparative Example 11) was obtained according to the method described in "A. Introduction of the amino group-containing compound into the polymer constituting the sea component", using the collected sea-island composite fiber of Comparative Example 10 as a knitted fabric (hereinafter, knitted fabric of Comparative Example 10). Further, 43 mL of a DETA reaction solution with a DETA concentration of 1 mM per 1 g of the knitted fabric of Comparative Example 11 was used to obtain an aminated knitted fabric (hereinafter, a knitted fabric of Comparative Example 12). Various tests were performed using the obtained knitted fabric of Comparative Example 10, knitted fabric of Comparative Example 11, and the knitted fabric of Comparative Example 12. The results are shown in Tables 3 and 4. The L/S values were from 0.4 to 0.5 $\mu m^{-1}$, and the distances from the fiber surface to the outermost island component were 1.0 µm for the knitted fabric of Comparative Example 10 and 1.0 µm or less for both the knitted fabric of Comparative Example 11 and the knitted fabric of Comparative Example 12. The charge densities of the knitted fabric of Comparative Example 10 and the knitted fabric of Comparative Example 11 were 0 µmol/g, and the charge density of the knitted fabric of Comparative Example 12 was 117 µmol/g. The island component exposure was 0 pieces/$mm^2$ for the knitted fabric of Comparative Example 10, and 31 pieces/$mm^2$ and 154 pieces/$mm^2$ for the knitted fabric of Comparative Example 11 and the knitted fabric of Comparative Example 12, respectively. The numbers of fine particles generated were 57 pieces/mL for the knitted fabric of Comparative Example 10, and 1,621 pieces/mL and 1,839 pieces/mL for the knitted fabric of Comparative Example 11 and the knitted fabric of Comparative Example 12, respectively. The latent TGF-β adsorption amounts were 4 ng/g for the knitted fabric of Comparative Example 10, 19 ng/g for the knitted fabric of Comparative Example 11, and 151 ng/g for the knitted fabric of Comparative Example 12 reacted with DETA.

Comparative Examples 13 to 15

A polymer alloy composed of 90% by weight of polystyrene and 10% by weight of polypropylene as the sea component and polypropylene as the island component were separately melted and metered into a spinning pack incorporating a sea-island composite spinneret having 6 island component distribution holes per discharge hole to form a sea-island composite flow and melted and discharged. The sea-island composite fiber (hereinafter, referred to as a sea-island composite fiber of Comparative Example 13) was collected by controlling the island ratio to 70% by weight. The fiber diameter was 20 µm. Further, α-chloroacetamidomethylated knitted fabric (hereinafter, referred to as the knitted fabric of Comparative Example 14) was obtained according to the method described in "A. Introduction of the amino group-containing compound into the polymer constituting the sea component", using the collected sea-island composite fiber of Comparative Example 13 as a knitted fabric (hereinafter, knitted fabric of Comparative Example 13). Further, 43 mL of a DETA reaction solution with a DETA concentration of 20 mM per 1 g of the knitted fabric of Comparative Example 14 was used to obtain an aminated knitted fabric (hereinafter, the knitted fabric of Comparative Example 15). Various tests were performed using the obtained knitted fabric of Comparative Example 13, the knitted fabric of Comparative Example 14, and the knitted fabric of Comparative Example 15. The results are shown in Tables 3 and 4. The L/S values were from 0.3 to 0.4 $\mu m^{-1}$, and the distances from the fiber surface to the outermost island component were 0.6 µm for the knitted fabric of Comparative Example 13 and 0.0 µm for both the knitted fabric of Comparative Example 14 and the knitted fabric of Comparative Example 15. The charge densities of the knitted fabric of Comparative Example 13 and the knitted fabric of Comparative Example 14 were 0 µmol/g, and the charge density of the knitted fabric of Comparative Example 15 was 280 µmol/g. The island component exposures were 0 pieces/$mm^2$ for the knitted fabric of Comparative Example 13, and 25 pieces/$mm^2$ and 23 pieces/$mm^2$ for the knitted fabric of Comparative Example 14 and the knitted fabric of Comparative Example 15, respectively. The numbers of fine particles generated were 27 pieces/mL for the knitted fabric of Comparative Example 13, and 600 pieces/mL and 519 pieces/mL for the knitted fabric of Comparative Example 14 and the knitted fabric of Comparative Example 15, respectively. The latent TGF-β adsorption amounts were 3 ng/g for the knitted fabric of Comparative Example 13, 18 ng/g for the knitted fabric of Comparative Example 14, and 209 ng/g for the knitted fabric of Comparative Example 15 reacted with DETA.

Comparative Examples 16 to 18

A polymer alloy composed of 90% by weight of polystyrene and 10% by weight of polypropylene as the sea component and polypropylene as the island component were separately melted and metered into a spinning pack incorporating a sea-island composite spinneret having 6 island component distribution holes per discharge hole to form a sea-island composite flow and melted and discharged. The sea-island composite fiber (hereinafter, referred to as a sea-island composite fiber of Comparative Example 16) was collected by controlling the island ratio to 50% by weight. The fiber diameter was 20 µm. Further, α-chloroacetamidomethylated knitted fabric (hereinafter, referred to as knitted fabric of Comparative Example 17) was obtained according to the method described in "A. Introduction of the amino group-containing compound into the polymer constituting the sea component", using the collected sea-island composite fiber of Comparative Example 16 as a knitted fabric (hereinafter, knitted fabric of Comparative Example 16). Further, 43 mL of a DETA reaction solution with a DETA concentration of 1 mM per 1 g of the knitted fabric of Comparative Example 17 was used to obtain an aminated knitted fabric (hereinafter, a knitted fabric of Comparative Example 18). Various tests were performed using the obtained knitted fabric of Comparative Example 16, the knitted fabric of Comparative Example 17, and the knitted fabric of Comparative Example 18. The results are shown in Tables 3 and 4. The L/S values were from 0.2 to 0.3 $\mu m^{-1}$, and the distances from the fiber surface to the outermost island component were 0.6 µm for the knitted fabric of Comparative Example 16 and 0.0 µm for both the knitted fabric of Comparative Example 17 and the knitted fabric of Comparative Example 18. The charge densities of the knitted fabric of Comparative Example 16 and the knitted fabric of Comparative Example 17 were 0 µmol/g, and the charge density of the knitted fabric of Comparative Example 18 was 95 µmol/g. The island component exposures were 0 pieces/$mm^2$ for the knitted fabric of Comparative Example 16, and 36 pieces/$mm^2$ and 62 pieces/$mm^2$ for the knitted fabric of Comparative Example 17 and the knitted fabric of Comparative Example 18, respectively. The numbers of fine particles generated were 33 pieces/mL for the knitted fabric of Comparative Example 16, and 1,063 pieces/mL and 1,174 pieces/mL for the knitted fabric of Comparative Example 17 and the knitted fabric of Comparative Example 18, respectively. The latent TGF-β adsorption amounts were 5 ng/g for the knitted fabric of Comparative Example 16, 17 ng/g for the knitted fabric of Comparative Example 17, and 120 ng/g for the knitted fabric of Comparative Example 18 reacted with DETA.

Comparative Examples 19 to 21

A polymer alloy composed of 90% by weight of polystyrene and 10% by weight of polypropylene as the sheath (sea) component and polypropylene as the core (island) component were separately melted and metered into a spinning pack incorporating a sheath-core composite spinneret and melted and discharged. The sheath-core composite fiber (hereinafter, referred to as a sheath-core composite fiber of Comparative Example 19) was collected by controlling the core ratio to 50% by weight. The fiber diameter was 20 μm. Further, α-chloroacetamidomethylated knitted fabric (hereinafter, referred to as knitted fabric of Comparative Example 20) was obtained according to the method described in "A. Introduction of the amino group-containing compound into the polymer constituting the sea component", using the collected sheath-core composite fiber of Comparative Example 19 as a knitted fabric (hereinafter, knitted fabric of Comparative Example 19). Further, 43 mL of a DETA reaction solution with a DETA concentration of 1 mM per 1 g of the knitted fabric of Comparative Example 20 was used to obtain an aminated knitted fabric (hereinafter, a knitted fabric of Comparative Example 21). Various tests were performed using the obtained knitted fabric of Comparative Example 19, the knitted fabric of Comparative Example 20, and the knitted fabric of Comparative Example 21. The results are shown in Tables 3 and 4. The L/S values were 0.1 $\mu m^{-1}$ in all cases, and the distances from the fiber surface to the outermost island component were from 1.8 to 3.1 μm. The charge densities of the knitted fabric of Comparative Example 19 and the knitted fabric of Comparative Example 20 were 0 μmol/g, and the charge density of the knitted fabric of Comparative Example 21 was 160 μmol/g. The island component exposures was 0 pieces/mm$^2$ for the knitted fabric of Comparative Example 19, and 29 pieces/mm$^2$ and 60 pieces/mm$^2$ for the knitted fabric of Comparative Example 20 and the knitted fabric of Comparative Example 21, respectively. The numbers of fine particles generated was 44 pieces/mL for the knitted fabric of Comparative Example 19, and 845 pieces/mL and 1,028 pieces/mL for the knitted fabric of Comparative Example 20 and the knitted fabric of Comparative Example 21, respectively. The latent TGF-β adsorption amounts were 4 ng/g for the knitted fabric of Comparative Example 19, 11 ng/g for the knitted fabric of Comparative Example 20, and 98 ng/g for the knitted fabric of Comparative Example 21 reacted with DETA.

Comparative Examples 22, 23, Example 9

Polystyrene as the sea component and polypropylene as the island component were separately melted and metered into a spinning pack incorporating a sea-island composite spinneret having 264 island component distribution holes per discharge hole to form a sea-island composite flow and melted and discharged. The sea-island composite fiber (hereinafter, referred to as a sea-island composite fiber of Comparative Example 22) was collected by controlling the island ratio to 50% by weight. The fiber diameter was 18 μm. Further, α-chloroacetamidomethylated knitted fabric (hereinafter, referred to as the knitted fabric of Comparative Example 23) was obtained according to the method described in "A. Introduction of the amino group-containing compound into the polymer constituting the sea component", using the collected sea-island composite fiber of Comparative Example 22 as a knitted fabric (hereinafter, knitted fabric of Comparative Example 22). Further, 43 mL of an amination reaction solution with a DETA concentration of 1 mM per 1 g of the knitted fabric of Comparative Example 23 was used to obtain an aminated knitted fabric (hereinafter, the knitted fabric of Example 9). Various tests were performed using the obtained knitted fabric of Comparative Example 22, the knitted fabric of Comparative Example 23, and the knitted fabric of Example 9. The results are shown in Tables 5 and 6. The L/S values were from 2.1 to 2.7 $\mu m^{-1}$, and the distances from the fiber surface to the outermost island component were 0.7 μm or less in all cases. The charge densities of the knitted fabric of Comparative Example 22 and the knitted fabric of Comparative Example 23 were 0 μmol/g, and the charge density of the knitted fabric of Example 9 was 305 μmol/g. The island component exposures were 7 pieces/mm$^2$ or less in all cases. The numbers of fine particles generated were 128 pieces/mL or less in all cases. The latent TGF-β adsorption amounts were 2 ng/g for the knitted fabric of Comparative Example 22, 9 ng/g for the knitted fabric of Comparative Example 23, and 92 ng/g for the knitted fabric of Example 9 reacted with DETA.

Comparative Examples 24, 25, Example 10

Polystyrene as the sea component and polypropylene as the island component were separately melted and metered into a spinning pack incorporating a sea-island composite spinneret having 264 island component distribution holes per discharge hole to form a sea-island composite flow and melted and discharged. The sea-island composite fiber (hereinafter, referred to as a sea-island composite fiber of Comparative Example 24) was collected by controlling the island ratio to 70% by weight. The fiber diameter was 20 μm. Further, α-chloroacetamidomethylated knitted fabric (hereinafter, referred to as the knitted fabric of Comparative Example 25) was obtained according to the method described in "A. Introduction of the amino group-containing compound into the polymer constituting the sea component", using the collected sea-island composite fiber of Comparative Example 24 as a knitted fabric (hereinafter, knitted fabric of Comparative Example 24). Further, 43 mL of an amination reaction solution with a DETA concentration of 1 mM per 1 g of the knitted fabric of Comparative Example 25 was used to obtain an aminated knitted fabric (hereinafter, the knitted fabric of Example 10). Various tests were performed using the obtained knitted fabric of Comparative Example 24, the knitted fabric of Comparative Example 25, and the knitted fabric of Example 10. The results are shown in Tables 5 and 6. The L/S values were from 2.3 to 2.6 $\mu m^{-1}$, and the distances from the fiber surface to the outermost island component were 0.8 μm or less in all cases. The charge densities of the knitted fabric of Comparative Example 24 and the knitted fabric of Comparative Example 25 were 0 μmol/g, and the charge density of the knitted fabric of Example 10 was 221 μmol/g. The island component exposures were 3 pieces/mm² or less in all cases. The numbers of fine particles generated were 94 pieces/mL or less in all cases. The latent TGF-β adsorption amounts were 4 ng/g for the knitted fabric of Comparative Example 24, 14 ng/g for the knitted fabric of Comparative Example 25, and 73 ng/g for the knitted fabric of Example 10 reacted with DETA.

Comparative Examples 26, 27, Example 11

Polystyrene as the sea component and polypropylene as the island component were separately melted and metered into a spinning pack incorporating a sea-island composite spinneret having 264 island component distribution holes per discharge hole to form a sea-island composite flow and melted and discharged. The sea-island composite fiber (hereinafter, referred to as a sea-island composite fiber of Comparative Example 26) was collected by controlling the island ratio to 30% by weight. The fiber diameter was 20 μm. Further, α-chloroacetamidomethylated knitted fabric (hereinafter, referred to as knitted fabric of Comparative Example 27) was obtained according to the method described in "A. Introduction of the amino group-containing compound into the polymer constituting the sea component", using the collected sea-island composite fiber of Comparative Example 26 as a knitted fabric (hereinafter, knitted fabric of Comparative Example 26). Further, 43 mL of an amination reaction solution with a DETA concentration of 1 mM per 1 g of the knitted fabric of Comparative Example 27 was used to obtain an aminated knitted fabric (hereinafter, a knitted fabric of Example 11). Various tests were performed using the obtained knitted fabric of Comparative Example 26, the knitted fabric of Comparative Example 27, and the knitted fabric of Example 11. The results are shown in Tables 5 and 6. The L/S values were from 1.4 to 1.9 μm⁻¹, and the distances from the fiber surface to the outermost island component were 0.7 μm or less in all cases. The charge densities of the knitted fabric of Comparative Example 26 and the knitted fabric of Comparative Example 27 was 0 μmol/g, and the charge density of the knitted fabric of Example 11 was 292 μmol/g. The island component exposure was 16 pieces/mm² or less. The numbers of fine particles generated was 190 pieces/mL or less in all cases. The latent TGF-β adsorption amounts were 2 ng/g for the knitted fabric of Comparative Example 26, 16 ng/g for the knitted fabric of Comparative Example 27, and 101 ng/g for the knitted fabric of Example 11 reacted with DETA.

TABLE 1

|  | Average total length (L) of perimeters of all the island components (μm) | Average cross-sectional area (S) (μm²) | L/S (μm⁻¹) | Distance from surface to outermost island component (μm) | Charge density (μmol/g) |
| --- | --- | --- | --- | --- | --- |
| Comparative Example 1 | 1216 | 330 | 3.7 | 0.7 | 0 |
| Comparative Example 2 | 1245 | 405 | 3.1 | 0.8 | 0 |
| Example 1 | 1300 | 403 | 3.2 | 0.7 | 11 |
| Example 2 | 1192 | 412 | 2.9 | 0.9 | 234 |
| Example 3 | 1117 | 436 | 2.6 | 0.8 | 273 |
| Example 4 | 1031 | 340 | 3.0 | 0.9 | 324 |
| Example 5 | 1126 | 388 | 2.9 | 0.7 | 187 |
| Example 6 | 1286 | 400 | 3.2 | 1.1 | 261 |
| Comparative Example 3 | 1544 | 415 | 3.7 | 0.1 | 0 |
| Comparative Example 4 | 1379 | 465 | 3.0 | 0.1 | 0 |
| Example 7 | 1462 | 547 | 2.7 | 0.1 | 497 |
| Comparative Example 5 | 1769 | 708 | 2.5 | 2.1 | 0 |
| Comparative Example 6 | 1724 | 865 | 2.0 | 1.9 | 0 |
| Example 8 | 1784 | 924 | 1.9 | 1.9 | 211 |

TABLE 2

|  | Island component exposure | | Number of fine particles generated | | Adsorption amount of latent type TGF-β | |
| --- | --- | --- | --- | --- | --- | --- |
|  | (pieces/mm²) | evaluation | (pieces/mL) | evaluation | (ng/g) | evaluation |
| Comparative Example 1 | 0 | ○ | 38 | ○ | 5 | x |
| Comparative Example 2 | 0 | ○ | 109 | ○ | 17 | x |
| Example 1 | 2 | ○ | 131 | ○ | 34 | ○ |
| Example 2 | 1 | ○ | 153 | ○ | 63 | ○ |
| Example 3 | 1 | ○ | 117 | ○ | 79 | ○ |
| Example 4 | 0 | ○ | 122 | ○ | 67 | ○ |
| Example 5 | 3 | ○ | 133 | ○ | 66 | ○ |
| Example 6 | 1 | ○ | 101 | ○ | 58 | ○ |
| Comparative Example 3 | 0 | ○ | 47 | ○ | 1 | x |

TABLE 2-continued

|  | Island component exposure | | Number of fine particles generated | | Adsorption amount of latent type TGF-β | |
| --- | --- | --- | --- | --- | --- | --- |
|  | (pieces/mm$^2$) | evaluation | (pieces/mL) | evaluation | (ng/g) | evaluation |
| Comparative Example 4 | 7 | ○ | 73 | ○ | 13 | x |
| Example 7 | 8 | ○ | 96 | ○ | 140 | ○ |
| Comparative Example 5 | 0 | ○ | 43 | ○ | 5 | x |
| Comparative Example 6 | 0 | ○ | 161 | ○ | 13 | x |
| Example 8 | 0 | ○ | 190 | ○ | 71 | ○ |

TABLE 3

|  | Average total length (L) of perimeters of all island components (μm) | Average cross-sectional area (S) (μm$^2$) | L/S (μm$^{-1}$) | Distance from surface to outermost island component (μm) | charge density (μmol/g) |
| --- | --- | --- | --- | --- | --- |
| Comparative Example 7 | 2123 | 701 | 3.0 | 2.4 | 0 |
| Comparative Example 8 | 2126 | 880 | 2.4 | 2.4 | 0 |
| Comparative Example 9 | 2267 | 896 | 2.5 | 2.2 | 162 |
| Comparative Example 10 | 170 | 327 | 0.5 | 1.0 | 0 |
| Comparative Example 11 | 176 | 392 | 0.4 | 0.0 | 0 |
| Comparative Example 12 | 174 | 384 | 0.5 | 0.1 | 117 |
| Comparative Example 13 | 139 | 366 | 0.4 | 0.6 | 0 |
| Comparative Example 14 | 135 | 495 | 0.3 | 0.0 | 0 |
| Comparative Example 15 | 150 | 455 | 0.3 | 0.0 | 280 |
| Comparative Example 16 | 115 | 350 | 0.3 | 0.6 | 0 |
| Comparative Example 17 | 101 | 462 | 0.2 | 0.0 | 0 |
| Comparative Example 18 | 114 | 451 | 0.3 | 0.0 | 95 |
| Comparative Example 19 | 46 | 339 | 0.1 | 3.1 | 0 |
| Comparative Example 20 | 44 | 399 | 0.1 | 1.8 | 0 |
| Comparative Example 21 | 48 | 411 | 0.1 | 1.8 | 160 |

TABLE 4

|  | Island component exposure | | Number of fine particles generated | | Adsorption amount of latent type TGF-β | |
| --- | --- | --- | --- | --- | --- | --- |
|  | (pieces/mm$^2$) | Evaluation | (pieces/mL) | Evaluation | (ng/g) | Evaluation |
| Comparative Example 7 | 0 | ○ | 36 | ○ | 0 | x |
| Comparative Example 8 | 0 | ○ | 394 | x | 14 | x |
| Comparative Example 9 | 0 | ○ | 355 | x | 90 | ○ |
| Comparative Example 10 | 0 | ○ | 57 | ○ | 4 | x |
| Comparative Example 11 | 31 | x | 1621 | x | 19 | x |
| Comparative Example 12 | 154 | x | 1839 | x | 151 | ○ |
| Comparative Example 13 | 0 | ○ | 27 | ○ | 3 | x |

TABLE 4-continued

|  | Island component exposure | | Number of fine particles generated | | Adsorption amount of latent type TGF-β | |
|---|---|---|---|---|---|---|
|  | (pieces/mm²) | Evaluation | (pieces/mL) | Evaluation | (ng/g) | Evaluation |
| Comparative Example 14 | 25 | x | 600 | x | 18 | x |
| Comparative Example 15 | 23 | x | 519 | x | 209 | ○ |
| Comparative Example 16 | 0 | ○ | 33 | ○ | 5 | x |
| Comparative Example 17 | 36 | x | 1063 | x | 17 | x |
| Comparative Example 18 | 62 | x | 1174 | x | 120 | ○ |
| Comparative Example 19 | 0 | ○ | 44 | ○ | 4 | x |
| Comparative Example 20 | 29 | x | 845 | x | 11 | x |
| Comparative Example 21 | 60 | x | 1028 | x | 98 | ○ |

TABLE 5

|  | Average total length (L) of perimeters of all island components (μm) | Average cross-sectional area (S) (μm²) | L/S (μm⁻¹) | Distance from surface to outermost island component (μm) | charge density (μmol/g) |
|---|---|---|---|---|---|
| Comparative Example 22 | 659 | 248 | 2.7 | 0.7 | 0 |
| Comparative Example 23 | 681 | 285 | 2.4 | 0.4 | 0 |
| Example 9 | 675 | 317 | 2.1 | 0.5 | 305 |
| Comparative Example 24 | 832 | 326 | 2.6 | 0.8 | 0 |
| Comparative Example 25 | 895 | 383 | 2.3 | 0.6 | 0 |
| Example 10 | 850 | 377 | 2.3 | 0.6 | 221 |
| Comparative Example 26 | 580 | 307 | 1.9 | 0.7 | 0 |
| Comparative Example 27 | 561 | 379 | 1.5 | 0.1 | 0 |
| Example 11 | 555 | 392 | 1.4 | 0.1 | 292 |

TABLE 6

|  | Island component exposure | | Number of fine particles generated | | Adsorption amount of latent type TGF-β | |
|---|---|---|---|---|---|---|
|  | (pieces/mm²) | Evaluation | (pieces/mL) | Evaluation | (ng/g) | Evaluation |
| Comparative Example 22 | 0 | ○ | 31 | ○ | 2 | x |
| Comparative Example 23 | 5 | ○ | 100 | ○ | 9 | x |
| Example 9 | 7 | ○ | 128 | ○ | 92 | ○ |
| Comparative Example 24 | 0 | ○ | 44 | ○ | 4 | x |
| Comparative Example 25 | 2 | ○ | 89 | ○ | 14 | x |
| Example 10 | 3 | ○ | 94 | ○ | 73 | ○ |
| Comparative Example 26 | 0 | ○ | 29 | ○ | 2 | x |
| Comparative Example 27 | 13 | ○ | 190 | ○ | 16 | x |
| Example 11 | 16 | ○ | 183 | ○ | 101 | ○ |

In Tables 1, 3, and 5, "average cross-sectional area (S)" means the average cross-sectional area (S) of a cross section perpendicular to the fiber axis of the sea-island composite fiber.

INDUSTRIAL APPLICABILITY

Since the sea-island composite fiber of the present invention is a ligand-immobilized fiber in which generation of fine particles is suppressed, such fiber can be utilized as a carrier for protein adsorption.

REFERENCE SIGNS LIST

A: Sea component
B: Island component
C: Sea-island composite fiber
a1: Shortest distance from fiber surface to outermost island component in one of six-divided fiber cross sections
a2: Shortest distance from fiber surface to outermost island component in one of six-divided fiber cross sections
a3: Shortest distance from fiber surface to outermost island component in one of six-divided fiber cross sections
a4: Shortest distance from fiber surface to outermost island component in one of six-divided fiber cross sections
a5: Shortest distance from fiber surface to outermost island component in one of six-divided fiber cross sections
a6: Shortest distance from fiber surface to outermost island component in one of six-divided fiber cross sections

The invention claimed is:

1. A sea-island composite fiber comprising a sea component and island components, wherein
   a value (L/S) obtained by dividing the average total length (L) of the perimeters of all the island components in a cross section perpendicular to the fiber axis by the average cross-sectional area (S) of the cross section is from 1.0 to 50.0 $\mu m^{-1}$,
   a distance from the surface of the sea-island composite fiber to the outermost island component is 1.9 μm or less, and
   an amino group-containing compound is covalently bonded to a polymer constituting the sea component at a charge density of 0.1 μmol or more and less than 500 μmol per 1 gram dry weight.

2. The sea-island composite fiber according to claim 1, wherein the L/S is from 1.4 to 50.0 $\mu m^{-1}$.

3. The sea-island composite fiber according to claim 1, wherein
   a main component of the polymer constituting the sea component is a polymer selected from the group consisting of polystyrene, polysulfone, polymethyl methacrylate, and their derivatives, and a polymer constituting the island components is a polyolefin.

4. The sea-island composite fiber according to claim 1, wherein the amino group-containing compound is ethylenediamine, diethylenetriamine, triethylenetetramine, or tetraethylenepentamine.

5. A carrier for protein adsorption comprising the sea-island composite fiber according to claim 1.

6. A medical column comprising the carrier for protein adsorption according to claim 5.

* * * * *